United States Patent [19]

Takeda et al.

[11] 4,329,507

[45] May 11, 1982

[54] SUBSTITUTED ARYL ETHYLENES

[75] Inventors: Makoto Takeda; Masayuki Uchide; Hiroshi Iwane, all of Amimachi, Japan

[73] Assignee: Mitsubishi Petrochemical Co., Ltd., Tokyo, Japan

[21] Appl. No.: 111,978

[22] Filed: Jan. 14, 1980

Related U.S. Application Data

[62] Division of Ser. No. 909,643, May 25, 1978, abandoned, which is a division of Ser. No. 734,592, Oct. 21, 1976, abandoned.

[30] Foreign Application Priority Data

Oct. 23, 1975 [JP] Japan .................................. 50/127787
Jul. 31, 1976 [JP] Japan .................................. 51/91523

[51] Int. Cl.$^3$ .......................................... C07C 49/794
[52] U.S. Cl. .................................... 568/332; 570/128; 568/635; 568/632; 549/388; 585/435; 562/406; 560/52; 560/56; 560/59; 560/75
[58] Field of Search ............... 568/635, 638, 639, 332; 585/435

[56] References Cited

U.S. PATENT DOCUMENTS

| | | | |
|---|---|---|---|
| 2,295,077 | 9/1942 | Dreisbach et al. .................. | 585/435 |
| 2,507,506 | 5/1950 | Dreisbach et al. .................. | 585/435 |
| 2,609,402 | 9/1952 | Salt et al. ............................ | 585/435 |
| 2,998,460 | 8/1961 | Olah et al. ........................... | 585/435 |
| 3,385,886 | 5/1968 | Nicholson et al. .................. | 562/465 |
| 3,600,437 | 8/1971 | Marshall ............................. | 560/11 |
| 3,641,127 | 2/1972 | Farge et al. ......................... | 562/426 |

FOREIGN PATENT DOCUMENTS

| | | | |
|---|---|---|---|
| 941387 | 2/1974 | Canada ................................ | 585/435 |
| 396079 | 7/1933 | United Kingdom ................ | 585/435 |

OTHER PUBLICATIONS

Rosenthale, Annual Reports in Med. Chem., vol. 8, pp. 214-223, (1973).
Rosenthale, Annual Reports in Med. Chem., vol. 10, pp. 172-181, (1975).
Lambardino et al., Aizneim Forsch, vol. 25, pp. 1629-1635, (1975).
David et al., Europ. Poly. J., vol. 12, pp. 71-76, (1976).
David et al., Europ. Poly. J., vol. 11, pp. 569-574, (1975).
Kulier et al., Chem. Abst., vol. 65, #13579a (1966).
Kulier et al., Chem. Abst., vol. 72, #78548r (1970).
Jarm et al., Chem. Abst., vol. 75, #21062k (1971).
Hickinbottom, "Reactions of Organic Compounds", p. 116, Wiley (1957).
Mowrey et al., J.A.C.S., vol. 68, pp. 1105-1109, (1946).
Kato, Chem. Abst., vol. 81, #153152y (1974).
Hueller et al., Chem. Abst., vol. 89, #110518v (1978).
David et al., Chem. Abst., vol. 85, #6193s (1976).
Hamayaki et al., Chem. Abst., vol. 87, #167732y (1977).
Emerson, Chem. Review, 1949, pp. 347-359.

Primary Examiner—Nicky Chan
Assistant Examiner—J. H. Reamer
Attorney, Agent, or Firm—Robert E. Burns; Emmanuel J. Lobato; Bruce L. Adams

[57] ABSTRACT

New substituted aryl ethylenes are disclosed which are produced by dehydration of the corresponding α- or β-(substituted aryl)ethyl alcohols or by dehydrohalogenation of the corresponding α- or β-(substituted aryl)ethyl halides.

3 Claims, No Drawings

SUBSTITUTED ARYL ETHYLENES

This is a divisional of application Ser. No. 909,643, filed May 25, 1978 now abandoned which is a Div. Appl. of Ser. No. 734,592 filed 10-21-76 now abandoned.

BACKGROUND OF THE INVENTION (1) Field of the Invention

This invention relates to new compounds, substituted aryl ethylenes and a process for producing the same and a process for producing α-(Substituted aryl)propionic acids which are derived from substituted aryl ethylene, have anti-inflammatory effect, antalgic effect and antipyretic effect and the precursors thereof, esters of α-(substituted aryl propionic acid.

(2) Description of the Prior Art

German Laid-Open Patent Publication No. 2426160 discloses compounds of the formula:

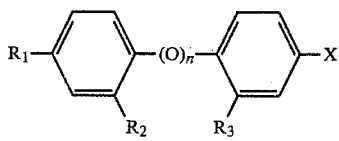

wherein n=0 or 1, X is an alkyl- or alkenyl group with 2 to 6 carbon atoms, and the residue $R_1$, $R_2$ and $R_3$ are the same or different and hydrogen, chlorine or fluorine atom and, when n=0, likewise bromine atom or a lower alkyl-, lower alkoxy-or hydroxy group, provided that at least one of the residues $R_1$, $R_2$ and $R_3$ is not hydrogen and, when n=0, at least one of the residues $R_2$ and $R_3$ is not hydrogen. The compounds are said to have valuable therapeutic properties including anti-inflammatory, analgesic and antifebrile properties. No examples are found of the compounds of the formula where X is vinyl.

SUMMARY OF THE INVENTION

An object of the present invention is to provide now substituted arylethylenes.

Other and further objects, features and advantages of the present invention will appear fully from the following description.

The compounds of the present invention represented by the general formula;

$$R^1\text{—CH}=\text{CH}_2 \qquad (I)$$

wherein, $R^1$ stands for 2-fluorobiphenylyl, 3-phenoxyphenyl, 3-benzoylphenyl or 4-isobutylphenyl represented by the general formula, $R^1$—CH=CH$_2$ ($R^1$ is the same as that defined above) with carbon monoxide in the presence of a lower alconol of the formula: $R^2OH$ where $R^2$ is a lower.

The substituted aryl ethylenes, can be readily prepared, for example, by dehydration or α- or β-(substituted aryl)ethyl alcohols or by dehydrohalogenation of α- or β-(substituted aryl)ethyl halides which are represented by the general formula,

wherein $R^1$ has the same meaning as that defined above, and one of X and Y stands for hydrogen and the other for hydroxyl or a halogen atom.

1. Substituted aryl ethyl alcohols or halides

The compounds represented by the general formula (II), which are suitable for the starting material for preparation of the substituted aryl ethylenes, include an α-(substituted aryl)ethyl alcohol, a β-(substituted aryl)ethyl alcohol, an α-(substituted aryl)ethyl halide, and a β-(substituted aryl)ethyl halide. In formula (II), the halogen atoms represented by X and Y are chlorine, bromine and iodine, and the substituent in the substituted aryl group $R^1$ is not especially limited as to its number and position for substitution as long as they are within the theoretical possibility.

These compounds represented by formula (II) can readily be prepared in the same way as in the processes for preparation of common aralkyl alcohols and aralkyl halides.

For example, an α-(substituted aryl)ethyl alcohol is prepared by reduction of the corresponding substituted aryl methyl ketone, or by reaction of the corresponding substituted aryl magnesium bromide with paraldehyde; and a β-(substituted aryl)ethyl alcohol is prepared by reduction of the corresponding substituted aryl acetic acid or an ester thereof, or by β-hydroxyethylation of the corresponding substituted aromatic compound with ethylene oxide via Friedel-Crafts reaction.

An α- or β-(substituted aryl)ethyl halide is prepared, for example, by halogenation of the corresponding substituted aryl alcohol or substituted aryl ethane with a halogenating agent, or by chloroethylation of the corresponding substituted aromatic compound with paraldehyde and hydrogen chloride.

Examples of the α- or β-(substituted aryl)ethyl alcohols or halides suitable for use in the present invention include: α- or β-(3-phenoxyphenyl)ethyl alcohol, α- or β-(4-isobutylphenyl)ethyl alcohol, α- or β-(4-benzoylphenyl)ethyl alcohol, α- or β-(2-fluoro-4-biphenylyl)ethyl bromide, chloride, α- or β-(2-xanthyl)ethyl α- or β-(3-benzoylphenyl)ethyl chloride, α- or β-(4-isobutylphenyl)ethyl chloride, α- or β-(4-isobutylphenyl)ethyl bromide, α- or β-(3-phenoxyphenyl)-ethyl chloride.

2. Dehydration or dehydrohalogenation step

The step of dehydration or dehydrohalogenation of the compounds represented by the general formula (II) to obtain the substituted arylethylenes (I) can be carried out in accordance with the methods for dehydration of known aryl ethyl alcohols or those for dehydrohalogenation of known aryl ethyl halides.

Some methods therefor are explained in the following.

These reactions proceed in a good yield and with less formation of by-products. The resulting substituted arylethylenes are stable compounds, and can generally be purified by means of a single distillation or re-crystallization to obtain the products with a sufficiently high purity, which can be used as the material for subsequent carbonylation step.

(1) Dehydration of α- or β-(substituted aryl)ethyl alcohols (2) Liquid-phase heating under atmospheric pressure An α- or β-(substituted aryl)ethyl alcohol and 1 to 20 moles, preferably 3 to 10 moles of dimethyl sulfoxide per mole of the alcohol are heated under atmospheric pressure at a temperature of 100° to 250° C., preferably

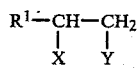

130° to 190° C., in the presence of 0.1–30% by weight, preferably 1–15% by weight of the alcohol of a polymerization inhibitor.

The polymerization inhibitor to be used is exemplified by hydroquinone, m-dinitrobenzene, N-nitrosodiphenylamine, picric acid, sodium sulfite, quinhydrone and the like.

(b) Liquid-phase heating under reduced pressure

Heating is generally carried out in the presence of a sulfate compound used as a dehydration accelerator.

As the sulfate compounds are employed sodium hydrogensulfate, potassium hydrogensulfate, potassium pyrosulfate and the like.

As a polymerization inhibitor is used the same one as in the above-mentioned step (a).

The alcohol is mixed with 0.01 to 10%, preferably 0.1 to 5% by weight of a sulfate compound and 0.1 to 30%, preferably 1 to 15% by weight of a polymerization inhibitor. The mixture is heated at a temperature of 100° to 280° C., preferably 195° to 250° C. under reduced pressure of 10 to 600 mmHg, preferably 20 to 400 mmHg.

(c) Gas-phase heating

Reaction is carried out in gaseous phase by contacting under heating the alcohol with an activated alumina or a caustic alkali.

Into a heated bed of an activated alumina or of a caustic alkali such as sodium hydroxide and potassium hydroxide, is introduced the alcohol under reduced pressure, or in the presence of a diluent gas such as nitrogen or carbon dioxide, or together with a volatile solvent such as an aromatic hydrocarbon or an ether, e.g. benzene, toluene, xylene or dioxane.

In case that an activated alumina is employed, it is suitable to heat the reaction system generally to 120° to 400° C., preferably 150° to 350° C., under a reduced pressure of 10 to 600 mmHg, preferably 20 to 400 mmHg, or in the presence of 1 to 40 moles and preferably 5 to 20 moles of a diluent gas such as nitrogen or carbon dioxide per mole of the alcohol or, when the alcohol is a solid, in the presence of 0.01 to 10 moles, preferably 0.1 to 5 moles, of a volatile solvent such as an aromatic hydrocarbon or an ether, e.g. benzene, toluene, xylene and dioxane per mole of the alcohol. In case that a caustic alkali is used, it is suitable to heat the reaction system to 100° to 250° C., preferably 120° to 200° C., under a reduced pressure of 2 to 200 mmHg, preferably 5 to 100 mmHg, or in the presence of 1 to 40 moles, preferably 5 to 20 moles, of a diluent gas such as nitrogen or carbon dioxide per mole of the alcohol or, when the alcohol is a solid, in the presence of 0.01 to 10 moles, preferably 0.1 to 5 moles, of a volatile solvent such as an aromatic hydrocarbon or an ether, e.g. benzene, toluene, xylene and dioxane per mole of the alcohol.

(2) Dehydrohalogenation of α- or β-(substituted aryl)ethyl halides (a) Heating together with a base The bases to be used are exemplified by organic bases such as pyridine, quinoline, piperidine, piperazine, aniline, N, N-dimethylaniline, and inorganic bases such as sodium hydroxide and potassium hydroxide.

Reaction is carried out by heating a mixture of the halide with 0.8 to 30 moles, preferably 1 to 15 moles, of the base per mole of the halide generally at a temperature of 0° to 260° C., preferably 20° to 220° C.

(b) Heating with an amine hydrochloride under reduced pressure

The amine hydrochloride to be used is a hydrochloride of a secondary or tertiary amine such as diamylamine hydrochloride, triamylamine hydrochloride, dihexylamine hydrochloride, and trihexylamine hydrochloride.

Reaction is carried out in gaseous phase by passing the halide through a molten amine hydrochloride heated at 150° to 300° C. and preferably 170° to 270° C., at a reduced pressure of 20 to 760 mmHg, preferably 50 to 200 mmHg, or in the presence of 1 to 40 moles, preferably 5 to 20 moles, of a diluent gas such as nitrogen or carbon dioxide per mole of the halide or, when the halide is a solid, in the presence of 0.01 to 10 moles, preferably 0.1 to 5 moles, of a volatile solvent such as an aromatic hydrocarbon or an ether, e.g. benzene, toluene, xylene and dioxane per mole of the halide.

3. Substituted aryl ethylenes

The substituted aryl ethylenes thus obtained are the compounds represented by the foregoing general formula (II).

Some compounds thereof are illustrated in the following table, which are believed to be novel compounds. The names of α-(substituted aryl) propionic acids obtained by carbonylation of the substituted aryl ethylenes are also shown in the table.

| Substituted aryl ethylenes | | Corresponding α-(substituted aryl) propionic acids |
|---|---|---|
| (1) | 2-fluoro-4-vinylbiphenyl 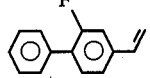 | α-(2-fluoro-4-biphenylyl) propionic acid |
| (2) | 3-phenoxystyrene 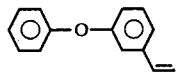 | α-(3-phenoxyphenyl) propionic acid |
| (3) | 3-vinylbenzophenone 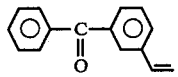 | α-(3-benzoylphenyl) propionic acid |
| (4) | 4-isobutylstyrene 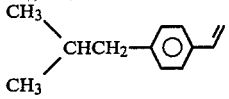 | α-(4-isobutylphenyl)-propionic acid |

EXAMPLE 1

In 750 ml. of carbon tetrachloride was dissolved 10 g of 2-fluoro-4-ethylbiphenyl. Then to the solution were added 10 g of N-bromosuccinimide and 0.1 g of benzoyl peroxide. After cooling, a solid substance was filtered off, and from the filtrate containing α-(2-fluoro-4-biphenylyl)ethyl bromide was distilled off the carbon tetrachloride. The residue thus obtained was dissolved in 500 ml. of ethyl alcohol, and then added with 17 g of potassium hydroxide. The resultant mixture was refluxed under heating for 1 hour. After cooling, the reaction mixture was poured into 2.5 l. of water, and then subjected to extraction with benzene. The benzene layer was washed with water, and dried with magnesium sulfate. The benzene in the layer was distilled off, and the resulting residue was subjected to column chromatography. From hexane eluate was obtained 5.5 g of 2-fluoro-4-vinylbiphenyl.

Yield: 56 mole %, refractive index $n_D^{25.5}$: 1.6119

Nuclear magnetic resonance spectrum (CCl$_4$) δ ppm
5.29: (1H, dd)
5.73: (1H, dd)
6.72: (1H, dd)
7.07–7.70: (8H, m)

EXAMPLE 2

In 250 ml. of dimethyl sulfoxide were dissolved 7.0 g of α-(3-phenoxyphenyl)ethyl alcohol and 0.5 g of m-dinitrobenzene as a polymerization inhibitor. The solution was subjected to reaction at 160° C. for 10 hours. After cooling, the reaction mixture was incorporated with 250 ml. of dichloromethane, and washed with 600 ml. of water. The resultant dichloromethane layer was separated after removal of the dimethyl sulfoxide, and dried with magnesium sulfate. Then the dichloromethane in the layer was distilled off under reduced pressure, and the resultant residue was subjected to column chromatography. From hexane eluate was obtained 4.75 g of 3-phenoxystyrene.

Yield: 75 mole %, $n_D^{24}$: 1.5980

Nuclear magnetic resonance spectrum (CDCl$_3$) δ ppm
5.26: (1H, dd)
5.72: (1H, dd)
6.67: (1H, dd)
6.75–7.52: (9H, m)

EXAMPLE 3

(1) To 6 g of α-(4-isobutylphenyl)ethyl alcohol were added 12 g of dimethyl sulfoxide and 0.1 g of m-dinitrobenzene as a polymerization inhibitor. The mixture was stirred at 160° C. for 8 hours. The resultant reaction liquor was cooled, diluted with water and then subjected to extraction with benzene. After the resulting organic layer was dried with magnesium sulfate, the solvent was distilled off. The residue thus obtained was distilled to give 4.2 g of 4-isobutylstyrene having the following physical properties.

Yield: 78 mole %
boiling point: 82–84° C./2.4 mmHg
colorless liquid, $n_D^{20}$ = 1.5218
Infrared absorption spectrum: 1625, 1381, 990, 904, 910 cm$^{-k}$
Nuclear magnetic resonance spectrum (in CDCl$_3$) δ ppm
0.89: (6H, c)
1.5–2.2: (1H, m)
2.42: (2H, d)
5.11: (1H, dd)
5.60: (1H, dd)
6.65: (1H, dd)
6.9–7.4: (4H, m)

Elemental analysis: theoretical: C: 89.94, H: 10.06.
found: C: 89.96, H: 9.92.

The 4-isobutylstyrene thus obtained was of a high purity, and could be used without further purification other than only a single distillation for subsequent reaction.

EXAMPLE 4

(1) To 20 g of α-(4-isobutylphenyl)ethyl chloride was added 80 ml. of pyridine, and the mixture was heated at 115° C. for 6 hours. The resultant product was poured into a mixture of 130 ml. of concentrated hydrochloric acid—370 g of ice, followed by extraction with chloroform.

After the chloroform solution thus obtained was dried with magnesium sulfate, the chloroform in the solution was distilled off. The resultant residue was further subjected to distillation to give 11.7 g of 4-isobutylstyrene. Yield: 65 mole %.

EXAMPLE 5

(1) Through a glass tube which was packed with alumina and heated at 270° C. were passed downward 1590 g of α-(4-isobutylphenyl)ethyl alcohol and nitrogen gas at a liquid hourly space velocity of 1.0 hr$^{-1}$ and space velocity of 2100 hr$^{-1}$. Effluent gas was collected by a receiver cooled with dry ice-methanol to give 1360 g of 4-isobutylstyrene.

Yield: 95 mole %

EXAMPLE 6

To 40 ml. of anhydrous tetrahydrofuran solution containing phenylmagnesium bromide prepared from 0.53 g of magnesium and 3.4 g of bromobenzene was added dropwise at room temperature 20 ml. of anhydrous tetrahydrofuran solution containing 2.3 g of 3-cyanostyrene. After agitation for 2 hours at room temperature, 30 ml. of 1 N aqueous hydrochloric acid was added dropwise to the tetrahydrofuran solution, and the resultant mixture was agitated for further 30 minutes.

The tetrahydrofuran layer was separated, washed with water, aqueous sodium hydrogen carbonate, and then water again, followed by drying with magnesium sulfate. Tetrahydrofuran was distilled off, and the residue was subjected to column chromatography.

From the benzene eluate was obtained 1.9 g of 3-vinylbenzophenone.

Yield: 51 mole %, $n_D^{24}$:1.6174

Nuclear magnetic resonance spectrum (CDCl$_3$) δ ppm
5.31: (1H, dd)
5.78: (1H, dd)
6.79: (1H, dd)
7.36–8.01: (9H, m)

While the present invention has been particularly shown and described with reference to preferred embodiments thereof, it will be understood by those skilled in the art that the foregoing and other changes and modifications can be made without departing from the spirit and scope of the invention.

We claim:
1. The compound of the formula

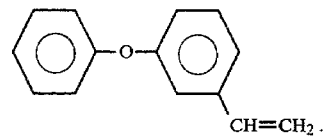

2. The compound of the formula

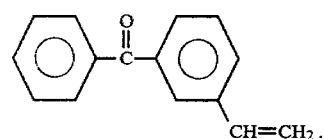

3. The compound of the formula

7
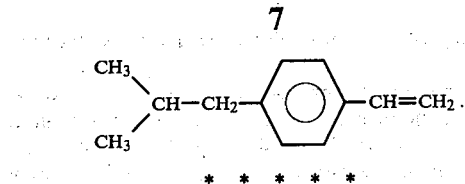
* * * * *
8
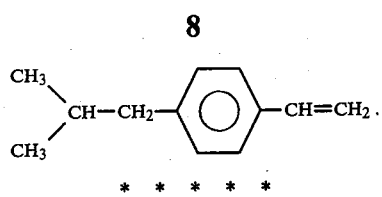
* * * * *